United States Patent [19]
Bothorel et al.

[11] Patent Number: 4,549,812
[45] Date of Patent: Oct. 29, 1985

[54] LIQUID PHASE COUNTER

[75] Inventors: Pierre Bothorel, Pessac; Roland Bernon, Cestas; Guy Gabriel, Pessac, all of France

[73] Assignee: Centre National de la Recherche Scientifique, Paris, France

[21] Appl. No.: 664,432

[22] Filed: Oct. 24, 1984

[30] Foreign Application Priority Data

Oct. 25, 1983 [FR] France ............... 83 16973

[51] Int. Cl.⁴ ........................... B01F 13/08
[52] U.S. Cl. ................... 366/142; 356/427; 366/273; 366/332
[58] Field of Search ............ 366/142, 143, 127, 273, 366/348, 349, 241, 332, 333, 334; 356/427, 426, 440, 436

[56] References Cited

U.S. PATENT DOCUMENTS

| | | |
|---|---|---|
| 2,971,371 | 2/1961 | Brennan et al. |
| 2,982,170 | 5/1961 | Wyss. |
| 3,972,614 | 8/1976 | Johansen ............... 366/142 |
| 4,125,327 | 11/1978 | Margolis ............... 356/427 |
| 4,227,815 | 10/1980 | Hoffa ............... 366/273 |
| 4,265,544 | 5/1981 | Banno ............... 356/427 |
| 4,293,643 | 10/1981 | Yukio ............... 366/142 |
| 4,390,283 | 6/1983 | Meyer ............... 366/142 |

FOREIGN PATENT DOCUMENTS

| | | |
|---|---|---|
| 2551260 | 5/1977 | Fed. Rep. of Germany. |
| 3203882 | 8/1983 | Fed. Rep. of Germany. |
| 2017936 | 10/1979 | United Kingdom. |

Primary Examiner—Robert W. Jenkins

[57] ABSTRACT

Liquid phase counter for a partly liquid, transparent mixture. This counter comprises at least one cell containing a transparent liquid mixture, means for homogenizing a mixture, means for the optical measurement of the transparency of the mixture, means for displacing the said means parallel to the cell, means for positioning said means to the right of a cell and an electronic control and processing means determining the number of phases of a mixture as a function of the signal supplied by the optical measuring means.

Application to the formation of the phase diagram of a partly liquid, transparent mixture.

6 Claims, 7 Drawing Figures

LIQUID PHASE COUNTER

BACKGROUND OF THE INVENTION

The present invention relates to a liquid phase counter making it possible to form the phase diagram of a partly liquid and transparent mixture. These diagrams are more particularly used in the oil industry, in the treatment of ores in an aqueous medium, in cosmetology, etc.

For example, in the field of oil, the counter according to the invention is used in the assisted recovery of petrol or gasoline. Since the first oil crisis in 1973, oil companies have attempted to improve the gasoline extraction efficiency, which is limited to 35% for technical and economic reasons. The process used consists of injecting into the oil well a monophase micro-emulsion, which, during the flushing of the well becomes a three-phase system. This micro-emulsion is constituted by a mixture containing at least a surfactant, pure or salt water, a hydrocarbon and optionally a cosurfactant, e.g. an alcohol. As a function of the proportions of each of the constituents of the mixture, the system can be at equilibrium, single, two, three or four-phase. Therefore, it is necessary to make a choice from among the mixtures so as to only retain those leading to an optimized three-phase system, which is the only one which can be used in the assisted recovery of gasoline.

No theoretical method is known for the a priori forming of the phase diagram and for consequently determining the mixtures which are of interest. Only the experimental study of a large number of mixtures makes it possible to select the useful mixtures, i.e. three-phase et equilibrium.

According to the prior art, the phase diagram of a mixture is produced manually. For this diagram to be accurate, it is necessary to plot the number of phases of a large number of points, which is very long. For example, the plotting of 15,000 points of this diagram takes several uninterrupted work years. Apart from the slowness, this process of producing a phase diagram is relatively inaccurate, the composition of each manually prepared mixture being itself of limited precision.

SUMMARY OF THE INVENTION

The object of the invention is to obviate these disadvantages. It relates to a liquid phase counter able to complete an initial partial mixing by adding the final liquid constituent or constituents, ensuring homogenization by stirring, observing whether the thermodynamic equilibrium is reached and counting the number of phases. This counter is able to deal with several mixtures at the same time, each of them being automatically diluted during this time.

Thus, the liquid phase counter comprises:

at least one cell fixed to a support, each cell being arranged vertically and containing a partly liquid and transparent mixture, a means for homogenizing the mixture of each cell, an optical means for measuring the optical transparency of the mixture between two walls of a cell, a displacement means for displacing the homogenization means and the measuring means over the entire height of a cell and parallel thereto, as well as a positioning means for positioning said means to the right of each cell, an electronic control and processing means supplying signals for controlling the displacement and positioning means and the homogenization means and able to determine the number of phases of a mixture according to the signals received from the optical measuring means.

The positioning means is only useful in the case of a counter with at least two cells.

In order to effect the plotting of the phase diagram of a partly liquid and transparent mixture, the counter also comprises, for each cell, at least one source of a liquid constituent of the mixture, a positive displacement pump for each source and electrovalves connecting said pump to each cell, said pump and said electrovalve being controlled by the electronic means.

According to a secondary feature, the cells are arranged on a circular ring, whose centre constitutes the axis of the positioning means.

According to another secondary feature, the optical measuring means comprises a lighting source and a facing photodiode arranged on either side of the cell.

According to another secondary feature, the homogenization means comprises an electromagnet and a magnetic bar.

According to another secondary feature, a permanent magnet is located in the cell or externally thereof above the mixture, constituting a rest position for the magnetic bar.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
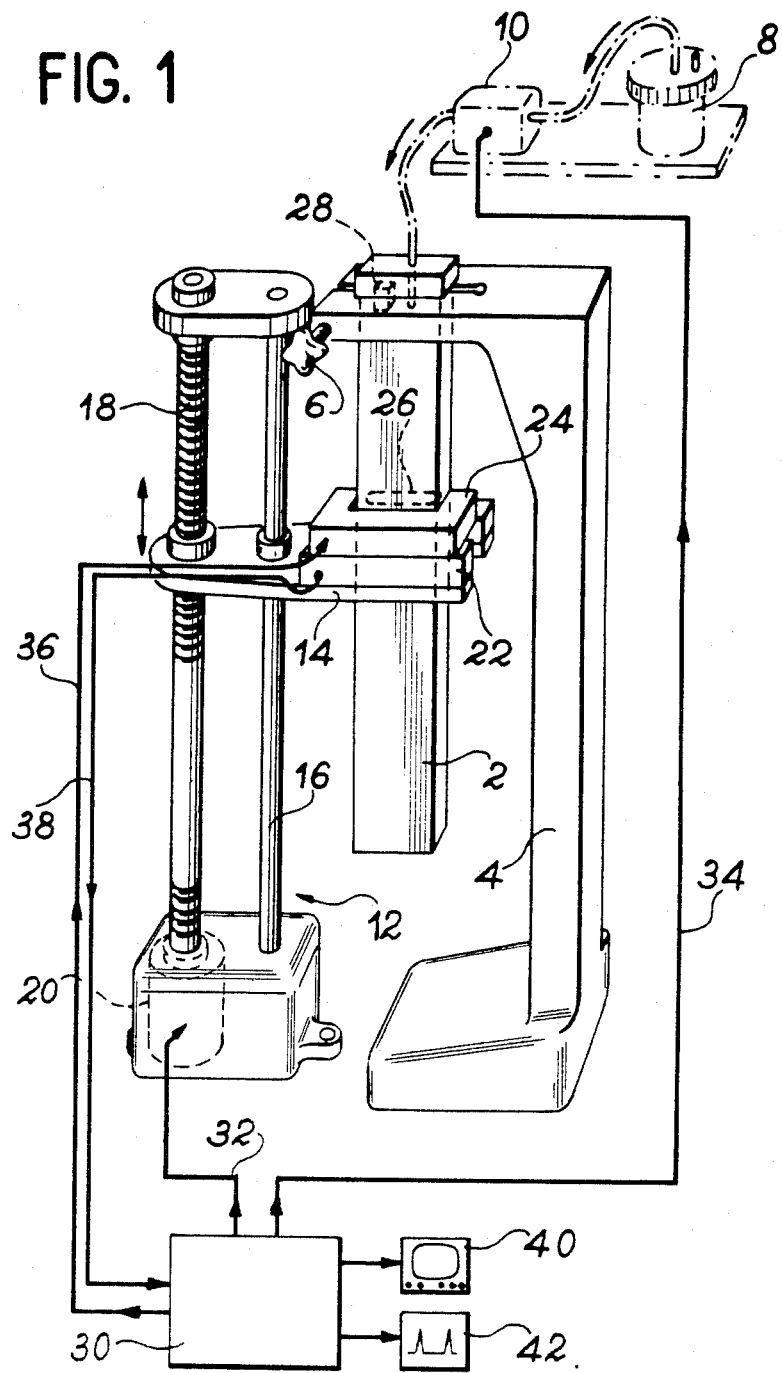
FIG. 1 an embodiment of a liquid phase counter with a single cell according to the invention.

FIG. 1 shows a single cell liquid phase counter according to the invention. It essentially comprises a parallelepipedic cell 2 containing the mixture to be analyzed, displacement means 12, an optical measuring means 22, a homogenization means 24 and an electronic control and processing means 30.

Cell 2 is maintained on a support 4 by an appropriate means, such as a screw 6. Close to the said support are also provided a source 8 of a liquid constituent of the mixture and a positive displacement pump 10. For example, the dimensions of the cell are 10 cm × 1 cm × 2 mm, the largest dimension being vertical.

The displacement means 12 makes it possible to displace a support 14 parallel to the cell 2 and over the entire height of said cell. It comprises a guide 16 for limiting the displacement of the support in the vertical axis and a screw controlled by a stepping motor 20 in order to accurately vertically displace said support.

Support 14 carries an optical measuring means 22 and a homogenization means 24 for the mixture. The optical measuring means has a lighting source and an optical transducer positioned on either side of the cell. The measurement by the optical tranducer of the transmission of the light beam which is passed through the cell makes it possible to determine whether the mixture is in equilibrium and to count the number of phases of said mixture. For example, homogenization means 24 is of the magnetic type. It can control the rotation in a vertical plane and/or the vertical displacement of a stirrer 26 arranged in the cell. During the measurement of the optical transmission, stirrer 26 is located in a rest position out of the mixture and is e.g. attached to a permanent magnet 28. This optical measuring means 22 and this homogenization means 24 will be described in greater detail with reference to FIGS. 3a and 3b.

Finally, the liquid phase counter comprises an electronic control and processing means 30, which by means of a connection 32 controls motor 20 of displacement means 12, by a connection 34 the starting up and the volume delivered by positive displacement pump 10 and by a line 36 the putting into operation of homogenization means 24. By a connection 38, it receives the signal supplied by the optical transducer of the optical measuring means 22. From this signal, it deduces the number of phases of the mixture contained in the cell. The signal received from the optical transducer can be displayed on a screen 40 or on a graphic output 42. For example, electronic means 30 is a microcomputer of type DEC LSI 11.

An explanation will now be given of the operation of this liquid phase counter. For example, reference will be made to the formation of a phase diagram of a partly liquid and transparent mixture used in the improved recovery of gasoline. Such a mixture has three or four constituents, which are a surfactant, a hydrocarbon, a solvent and optionally a cosurfactant, which is often formed by an alcohol.

A partial mixture containing all the constituents, with the exception of one or more of the liquid constituents is prepared manually and injected into the cell. In the case of the drawing, only one liquid constituent is absent from the mixture, is placed in source 8 and is, for example, the solvent.

The electronic means 30 will firstly control a homogenization of the mixture in the cell, by activating the homogenization means 24 and/or the motor 20. Electronic means 30 then controls the placing of stirrer 26 in the rest position 28 and then waits for the thermodynamic equilibrium of the mixture.

This thermodynamic state of the mixture is observed by the signals received from the optical transducer of the optical measuring means 22. For as long as equilibrium is not reached, the mixture is turbid and consequently the optical transmission low.

After a decanting waiting time of predetermined duration, the electronic means 30 controls the displacement of measuring means 22 over the entire height of the cell via motor 20. The signal received on connection 38, corresponding to the lighting signal received by the optical transducer during this displacement is then processed, particularly digitized and stored, by electronic means 30. The number of phases is then deduced from this process signal.

The display on screen 40 or on the graphic output 42 of the signal received enables an operator to check that the plotted number of phases is correct. This check can take place with a time delay, because the signal is stored.

When the number of phases of the mixture has been counted, the electronic means 30 controls by means of connections 34, the injection of a given volume of the liquid constituent from source 8 into cell 2. The latter then contains a new mixture on the basis of the proportion of its constituents, which is dealt with in the same way as the previous mixture.

By successive injections over a period of time, of given volumes of the liquid constituent from source 8, the counter according to the invention makes it possible, without human intervention, a large number of points of the phase diagram. Thus, the said liquid phase counter permits a rapid, precise and automatic plotting of a phase diagram of a partly liquid, transparent mixture.

Figure 2:
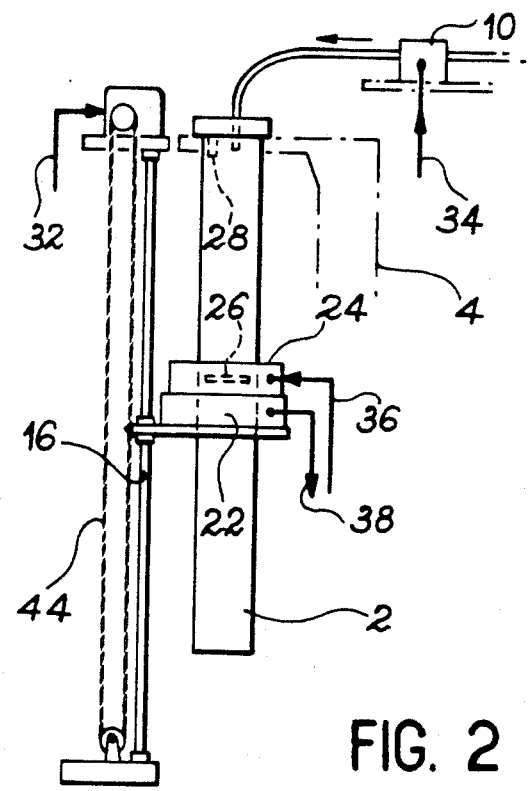
FIG. 2 a variant of the counter according to the invention.

FIG. 2 shows a variant of the embodiment of the liquid phase counter according to FIG. 1. Elements identical to those of FIG. 1 are given the same references. This embodiment differs from that of FIG. 1 in that screw 18 has been replaced by a cable 44 in displacement means 12.

Figure 3A:
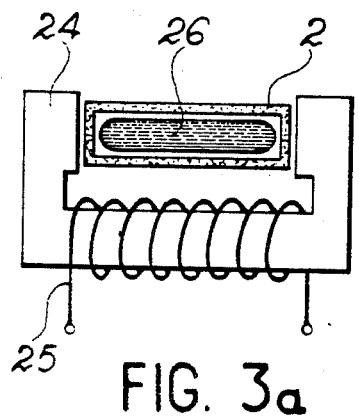
FIG. 3a a section of the homogenization means in plan view.
Figure 3B:
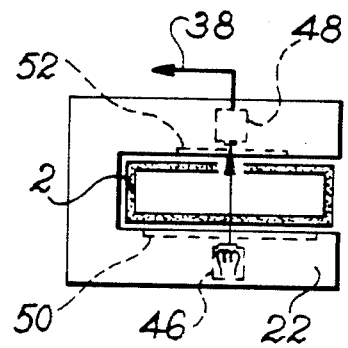
FIG. 3b a section of the optical measuring means in plan view.

FIGS. 3a and 3b show in section and in plan view, the homogenization means and the optical measuring means.

The homogenization means 24 is a U-shaped electromagnet energized by a current passing through the electrical coil 25 and whose air gap is occupied by cell 2. Stirrer 26 is constituted by a small magnetized bar, chemically insulated from the medium by a polymer sheath, e.g. made from polyethylene. The automation of homogenization by stirring is very difficult, because in the presence of surfactants, it is easy for froth to form. To prevent this, it is necessary to use this magnetic stirrer carefully.

To this end, the electronic control means 30 can control the passage of an alternating electric current of rapid or low frequency into the coil 25 thus bringing about a slow or fast rotation of stirrer 26 or a direct current for the purpose of immobilizing the stirrer. Simultaneously, by controlling motor 20, it is possible to vertically displace the stirrer. By combining the two controls, it is possible to displace the stirrer without rotation, which makes it possible to lick the walls of the cell in order to entrain possible liquid droplets or solid particles.

The optical measuring means 22 shown in FIG. 3b comprises a lighting source 46 and a facing optical transducer 48, said two elements being separated by cell 2. In order to detect the interface between these two liquid cells, it is appropriate for the resolution of the optical measuring means to be high. For this purpose, it has a 0.3 mm high slot 50 positioned in front of lighting source 46 and a 0.07 mm high slot 52 in front of the optical transducer 48. This optical measuring means makes it possible to distinguish the passage in front of an interface between two phases with an accuracy of about one tenth of a millimeter.

Figure 4:
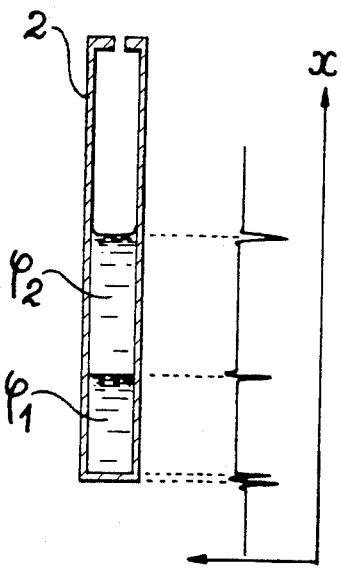
FIG. 4 the signal supplied by the optical transducer corresponding to the mixture contained in the cell.

The signal supplied by the optical transducer 48 is supplied by connection 38 to processing means 30. This signal is represented on FIG. 4 corresponding with a two-phase mixture contained in cell 2. The graph represents the transmission as a function of the position x. The four peaks respectively correspond to the air-glass interface of the cell, to the interface of the cell glass-phase $\phi_1$ of the mixture, to the interface of phases $\phi_1$ and $\phi_2$ of the mixture and to the interface of phase $\phi_2$ and air. This graph is supplied onto a display screen or a graphic output, in order that the user can carry out a check of the number of phases detected by the counter.

Figure 5:
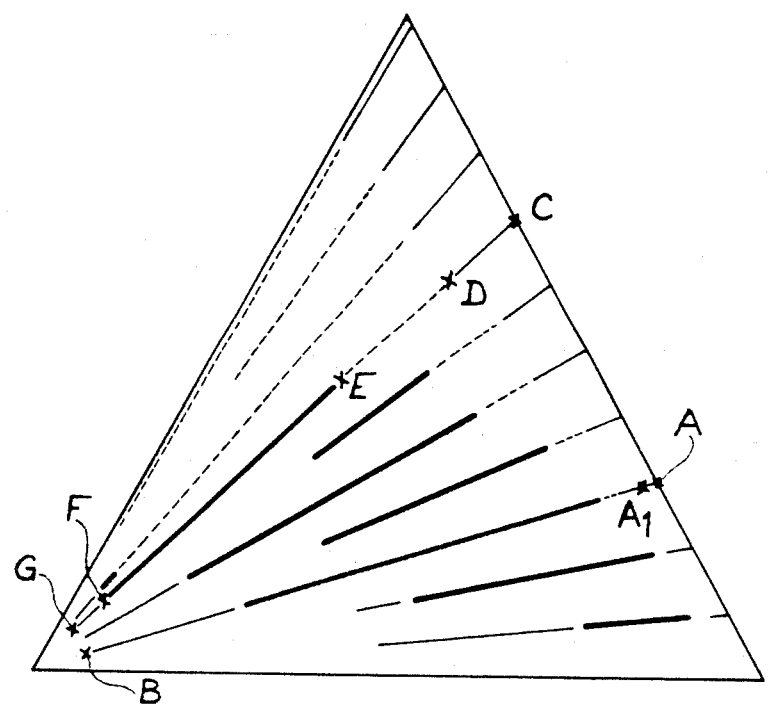
FIG. 5 a phase diagram obtained by the liquid phase counter according to the invention.

FIG. 5 represents a phase diagram obtained with a counter according to the invention. This investigated mixture consists of a solvent (water), a hydrocarbon (dodecane), a surfactant (octyl-benzene-sodium sulphate), OBS and a cosurfactant (butanol). The ratio of the proportions between the butanol and the OBS is equal to 2.

The diagram has been formed in the following manner. An initial partial mixture, without water, of composition A has been prepared. After counting the number of phases in this mixture, a volume of water is added thereto. The composition of this new mixture is represented by point $A_1$. The number of phases of this mixture has also been counted. By successive injections of volumes of water, the counter has thus counted the number of phases of a large number of mixtures located on the line segment AB.

Starting from a different initial composition, such as C, it determines the number of phases of a large number of mixtures located on line segment CG. The phase diagram is obtained by plotting an adequate number of line segments, such as AB and CG.

In the diagram of FIG. 5, the single line such as shown between points C and D or F and G correspond to photophase mixtures containing, after a given waiting time following a stirring of the mixture, one or more opaque phases (presence of a solid or an emulsion). Between points D and E, the mixture is single-phase and between points E and F it is two-phase. The mixtures which can be used in the improved recovery of gasoline are single-phase mixtures represented in dotted line form in the diagram.

The counter of FIG. 1 makes it possible to obtain this diagram with very high accuracy, due to the automatic dilution of the mixture in the cell and with a significant time gain compared with the prior art.

However, this counter has a by no means negligible lost time, due to the time necessary for waiting for the mixture to decant after homogenization. This counter lost time can be advantageously used for treating other cells, e.g. for diluting a mixture or for counting the number of phases of a mixture.

Figure 6:
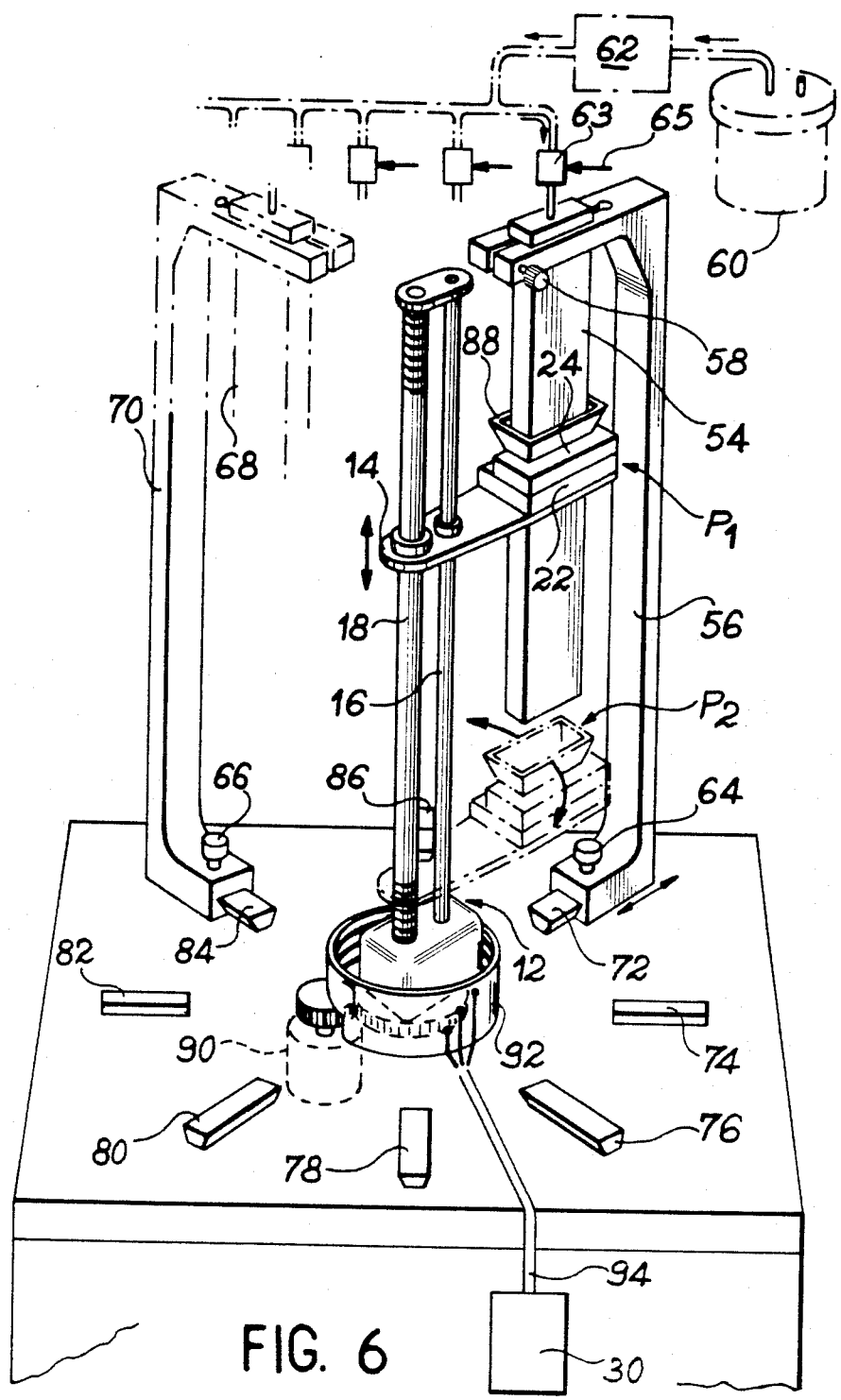
FIG. 6 a liquid phase counter according to the invention having several cells.

The multi-cell liquid phase counter of FIG. 6 makes it possible to considerably reduce this lost time.

The cells are arranged on a ring, whose centre coincides with the rotation axis of support 4. For example, the counter comprises 8 cells $C_1 \ldots C_i \ldots C_8$. One of the cells is shown in FIG. 6 as 54. It is fixed to a support 56 by a screw 58. Support 56 can be manually displaced in a radial direction on dovetail 72. A screw 64 fixes the support in the chosen position.

A source 60 of a liquid constituent of the mixture and a positive displacement pump 62 are also provided. An electrovalve 63 controlled by a connection 65 by electronic means 30 connects pump 62 to cell 54. At the outlet, the pump has several branches for supplying several cells. Other sources such as 60 containing other liquid constituents can be provided.

Another cell 68 and its support 70 are sketched in. It is also possible to see the dovetail 84 guiding the displacement of support 70 and the corresponding set screw 66. The six other dovetails 74, 76, 78, 80, 82 and 86 indicate the position of other cell-support assemblies.

The counter functions in the following manner. An initial partial mixture is manually prepared in each of the cells. The liquid constituents to be added can be contained in the source associated with each cell and added thereto with the aid of an associated pump, or can be contained in a source which is commom to several cells, a pump associated with the source supplying to each cell the liquid constituent by means of an electrovalve controlled by electronic means 30 and associated with each cell.

Electronic means 30 firstly controls the positioning of support 14 to the right of cell $C_1$ in position $P_2$, which is carried out by positioning means 90. The engagement of the support in the cell and position $P_1$ is facilitated by an inlet cone or funnel 88 located above the homogenization means 24. Electronic means 30 then carries out the homogenization of the mixture of cell $C_1$ by activating homogenization means 24 and displacement means 12 by line 94. The latter is connected to a ring 92 having three electrical connections identical to connections 32, 36 and 38 of FIG. 1. The stirrer is then brought into the rest position and the support 14 is disengaged from the cell. During the decanting of the mixture of cell $C_1$, the electronic means 30 successively homogenizes the mixtures of cell $C_2, C_3 \ldots C_8$.

Thus, active use is made of the waiting time for return to thermodynamic equilibrium of a mixture following homogenization and which constitutes lost time in the case of a single cell counter.

The gain of time compared with a single cell counter is significant. It is optimum and equal to the number of cells, if the time taken for decanting the mixture from a cell into a multi-cell counter is equal to the time necessary for said counter to homogenize the mixture of all the other cells.

What is claimed is:

1. A liquid phase counter for a partly liquid and transparent mixture, wherein it comprises:
   at least one cell fixed to a support, each cell being arranged vertically and containing a partly liquid and transparent mixture,
   a means for homogenizing the mixture of each cell,
   an optical means for measuring the optical transparency of the mixture between two walls of a cell,
   a displacement means for displacing the homogenization means and the measuring means over the entire height of a cell and a parallel thereto, as well as a positioning means for positioning said means to the right of each cell,
   an electronic control and processing means supplying signals for controlling the displacement and positioning means and the homogenization means and able to determine the number of phases of a mixture according to the signals received from the optical measuring means.

2. A counter according to claim 1 for plotting the phase diagram of a partly liquid, transparent mixture, wherein it also comprises for each cell:
   one or more sources, each supplying one constituent of the mixture,
   at least one pump per source,
   electrovalve controlled by the electronic means to permit the addition of each liquid constituent to each cell.

3. A counter according to claim 1, wherein the cells are located on a circular ring, whose centre constitutes the axis of the positioning means.

4. A counter according to claim 1, wherein the optical measuring means comprises a lighting source and a facing photodiode arranged on either side of the cell.

5. A counter according to claim 1, wherein the homogenization means comprises an electromagnet and a magnetic bar.

6. A counter according to claim 5, wherein a permanent magnet is located in the cell or outside the same, above the mixture, constituting a rest position for the magnetic bar.

* * * * *